United States Patent [19]

King

[11] Patent Number: 5,028,725

[45] Date of Patent: Jul. 2, 1991

[54] THIOLACTONE METAL COMPLEXES

[75] Inventor: Patrick F. King, Quincy, Mass.

[73] Assignee: Polaroid Corporation, Cambridge, Mass.

[21] Appl. No.: 447,154

[22] Filed: Dec. 7, 1989

Related U.S. Application Data

[60] Division of Ser. No. 935,533, Dec. 5, 1986, abandoned, which is a continuation-in-part of Ser. No. 809,157, Dec. 16, 1985, abandoned.

[51] Int. Cl.$^5$ .................. C07F 1/10; C07F 1/12; C07F 3/10; C07F 15/00
[52] U.S. Cl. .................. 556/113; 536/110; 536/114; 536/115; 536/118; 556/121; 556/122; 556/130; 556/131; 556/132; 556/136; 549/52; 549/210; 546/6
[58] Field of Search ............... 556/113, 114, 110, 112, 556/116, 117, 118, 121, 122, 130, 131, 132, 136; 549/55, 51, 54, 56, 57, 52, 210; 546/6

[56] References Cited

U.S. PATENT DOCUMENTS

| | | | |
|---|---|---|---|
| 2,043,081 | 6/1937 | Wahl et al. | 549/55 |
| 2,097,435 | 7/1937 | Austin et al. | 549/52 |
| 3,390,160 | 6/1968 | Heller et al. | 556/113 X |
| 3,471,537 | 10/1969 | Berke | 556/114 |
| 3,489,800 | 1/1970 | Tewksbury et al. | 564/317 |
| 3,499,887 | 3/1970 | Cooper et al. | 556/114 X |
| 3,919,277 | 11/1975 | Luhowy et al. | 556/113 |
| 3,928,477 | 12/1975 | Field et al. | 556/113 X |
| 4,213,784 | 7/1980 | Ikenoue et al. | 556/113 X |

FOREIGN PATENT DOCUMENTS

87/03541 6/1987 PCT Int'l Appl.
1417382 12/1975 United Kingdom.

OTHER PUBLICATIONS

March et al., Textbook "Advanced Organic Chemistry", McGraw-Hill, Inc., 1977, p. 349.
Merck et al., The Merck Index, 1976, Merck & Co., Inc. Rahway, N. J., p. 941.
Ernst et al., C. A. vol. 83, 1975, 83:163837f, p. 516.
Gilman, Henry, Org. Chem. An Advanced Treatise, vol. III, John Wiley and Sons, N. Y. 1953, pp. 247–55.
R. Meyer, Ber. 33, pp. 2570–2576, (and Translation).
R. Meyer, Ber 33, pp. 2577–2583, (and Translation).
Soloveichik et al., Zhurnal Org. Khi., vol. 10, No. 3, pp. 615–618, Mar. 1974 (Translation Only).
O'Brochta et al., J. Am. Chem. Soc., 61, pp. 2765–2768 (1939).
Stadler, P. A., Helvitica Chimica Acta, vol. 61, Fasc. 5 (1978), No. 162, p. 1675 (and Translation).
Chandrasekaran et al., Synthetic Communications, 12(9), pp. 727–731 (1982).
Kaloustian, et al., Tetrahedron Letters, vol. 22, pp. 413–416 (1981).

*Primary Examiner*—Arthur C. Prescott
*Attorney, Agent, or Firm*—Stanley H. Mervis

[57] ABSTRACT

This invention relates to novel compounds which are precursors for di- and triarylmethane dye precursor compounds possessing a thiolactone, dithiolactone or thioether ring-closing moiety.

10 Claims, No Drawings

THIOLACTONE METAL COMPLEXES

This application is a division of copending U.S. application Ser. No. 935,533 filed Dec. 5, 1986 (now abandoned), which application is a continuation-in-part of copending U.S. patent application Ser. No. 809,157 filed Dec. 16, 1985 (now abandoned).

BACKGROUND OF THE INVENTION

1. Field of the Invention

This invention relates to novel dye precursor compounds, to certain metal complexes thereof and to a method of synthesizing certain of the dye precursor compounds.

2. Background Art

Gilman, Henry, Organic Chemistry, An Advanced Treatise, Vol. III, John Wiley & Sons, New York, 1953, pp. 247-55 reviews organic dyes including the general concepts of, and early and modern theory regarding the relationship between color and chemical constitution. As discussed therein, a chromophore called a chromogene may be colored but does not yet represent a dye. To achieve this a further introduction of salt-forming groups, "auxochromes", into the molecule is required. The function of chromophore and auxochrome groups according to modern theory is necessary for modifying the molecule so as to introduce the possibility of resonance and thus color.

Although 3,3-disubstituted thiophthalides and dithiophthalides have been disclosed previously, none of the triarylmethane compounds described are dye precursors, i.e., color formers, since they do not exhibit the color-forming properties of dyes. In particular, R. Meyer, Ber. 33, pp. 2570-2576 and R. Meyer and J. Szanecki, ibid, pp. 2577-2583 disclose the synthesis of 3 3-dithiofluorane, dithiophenylphthalide (3,3-diphenylthiophthalide) and dithiodichlorofluorane by fusing the corresponding phthalides with phosphorus pentasulfide. The 3.3-dithiofluorane and the dithiodiphenylphthalide lack the auxochromic substituents necessary to complete the auxochromophoric system of a triarylmethane dye. The dithiodichlorofluorane also does not exhibit the properties of a dye, presumably because the chloro groups are not providing an auxochromic effect. I. P. Soloveichik, et al., Zhurnal Organicheskoi Khimii, Vol. 10, No. 3, pp. 615-618, March, 1974 disclose the preparation of 3,3-diphenylthiophthalide by reacting the 3,3-diphenyldithiophthalide of Meyer and Szanecki with mercuric acetate and also by reacting o-benzoylbenzoic acid and phosphorus pentasulfide followed by phenylation with the Friedel-Crafts reaction as previously described by I. O'Brochta, et al., J. Am. Chem. Soc., 61, 2762 (1959). U.S. Pat. No. 2,097,435 discloses a synthesis for thiophthalides including 3,3-diphenylthiophthalide by reacting the corresponding phthalide with sodium hydrosulfide under anhydrous conditions in the absence of air or oxygen. Like the 3,3-diphenyldithiophthalide discussed above, 3,3-diphenylthiophthalide is not a dye precursor since the 3,3-phenyl moieties lack an auxochromic substituent to impart dye properties.

SUMMARY OF THE INVENTION

The present invention is concerned with a new class of di- and triarylmethane compounds possessing certain S-containing ring-closing moieties which are dye precursor compounds. Specifically, the subject dye precursors are color-forming di- and triarylmethane compounds possessing a thiolactone or dithiolactone ring-closing moiety, e.g., a thiophthalide or dithiophthalide ring-closing moiety or a thioether ring-closing moiety. This invention also is concerned with certain metal complexes of the subject dye precursor compounds and in a further embodiment is concerned with a method of synthesizing the thiolactone compounds.

Unlike the color-forming triarylmethane compounds possessing a phthalide ring-closing moiety as exemplified by Crystal Violet Lactone, the tniolactone and dithiolactone dye precursors of the present invention as exemplified by thiophthalides and dithiophthalides do not undergo coloration with Bronsted acids (proton donors) but undergo coloration with Lewis acids (electron pair acceptors). With Bronsted acids, the subject thiolactone and dithiolactone dye precursors can form colorless acid salts but with Lewis acids, particularly $Ag^+$, and $Hg^{++}$, they undergo coloration by ring-opening to form a complex. The subject thioether dye precursors also exhibit sensitivity to Lewis acids, particularly $Ag^+$, and readily undergo coloration by ring-opening to form a silver complex. Because of their specific sensitivity to Lewis acids, the subject dye precursors find a variety of uses, for example, as analytical tools in colorimetric determinations and related applications and as color formers in image recording materials. Indeed, the ability of the subject dye precursors to form a colored dye almost instantaneously when contacted with $Ag^+$ renders these compounds eminently suitable for use as color formers in reactions employing silver salts including imaging systems employing inorganic silver salts, such as, silver halides and particularly imaging systems employing organic silver salts, such as silver behenate. In systems of the latter type, color formation is particularly efficient since it is effected by a phase change, i.e., effected by melting of the organic silver salt to provide the $Ag^+$ necessary for coloration rather than requiring a change of state.

The silver and other metal complexes of the subject di- and triarylmethane compounds are themselves useful as analytical tools and may be used in other applications as well. For example, they may be used in colorimetric analyses for determining the presence of halide or other ion having a stronger complexing ability with $Ag^+$ or $Hg^{++}$ than the thiolactone, dithiolactone or thioether moiety.

It is, therefore, one object of the present invention to provide novel color-forming compounds and certain metal salts thereof.

It is a further object of the present invention to provide a method of synthesizing the novel thiolactone color-forming compounds.

Other objects of the invention will in part be obvious and will in part appear hereinafter.

The invention accordingly comprises the methods involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

As noted above, the present invention is concerned with novel dye precursors, namely, novel color-forming di- and triarylmethane compounds possessing certain S-containing ring-closing moieties and with certain metal complexes thereof. Specifically the novel color-forming compounds of the present invention comprise a di- or triarylmethane dye precursor compound possessing within its di- or triarylmethane structure an aryl group substituted in the ortho position to the meso carbon atom with a thiolactone, dithiolactone or thioether moiety ring-closed on the meso carbon atom. When contacted with a Lewis acid material capable of opening the thiolactone, dithiolactone or thioether moiety, the compound is rendered colored, i.e., converted to its chromophore color which is a function of the auxochromophoric system of the di- or triarylmethane dye.

The Lewis acid material may be an organic or inorganic electron pair acceptor, and such materials suitable for a given thiolactone, dithiolactone or thioether dye precursor may be determined empirically. In this regard, it will be understood that the thiolactone, dithiolactone and thioether dye precursors do not react with all Lewis acids but that each thiolactone, dithiolactone and thioether reacts with at least one Lewis acid. Where both sulfur and oxygen are present in the ring-closed moiety as in the thiolactones, Lewis acid materials such as boron trifluoride etherate and aluminum chloride may be employed, but preferably, the Lewis acid material selected for both the thiolactones and dithiolactones and for the thioethers has a strong preference for coordinating with sulfur such as the metal ions classified as "soft acids" by Pearson, Ralph G., Hard and Soft Acids and Bases, Chem. Brit., 1967, 3, (3), p. 103. Preferably, the metal ion is that of a heavy metal, such as silver, gold, mercury and palladium. Silver is particularly preferred because of its exceptional ability for complexing with the thiolactone, dithiolactone and thioether moieties.

Contacting the dye precursor and Lewis acid material may be achieved in any suitable and convenient manner as desired for a given color-forming application, for example, by admixing solutions of the two components or by applying the Lewis acid material in liquid, gaseous, melted or other fluid form to the dye precursor coated on or absorbed into a substrate. Also, color formation may be effected imagewise. As an illustration, the dye precursor may be disposed in a layer and a solution of the Lewis acid material applied imagewise by coating through a stencil, spraying in an imagewise pattern, etc. or a Lewis acid material such as $Ag^+$ may be provided imagewise as a function of processing a selectively exposed photosensitive silver halide layer adjacent the dye precursor layer by applying an aqueous processing composition.

Rather than applying a solution, the Lewis acid material and dye precursor may be used in "dry" systems. They may be used as solids or one or both may be encapsulated and contained in a single sheet in the same or different layers or contained in separate superposed sheets, and color formation brought about in an imagewise fashion by the imagewise application of heat, pressure or other stimulus necessary to effect imagewise contact between the two components. In systems employing two sheets, the dye precursor may be coated in a binder on one sheet and the Lewis acid material coated in a binder on the other and heat applied imagewise to the superposed sheets to effect melting and contact of the two components, or a sheet coated with a layer of dye precursor encapsulated in oil may be superposed with the second sheet coated with Lewis acid material, and pressure applied imagewise to the superposed sheets to rupture the capsule walls and effect contact between the two components.

In a preferred embodiment, the two components are contained in the same sheet, that is, a single support carries the dye precursor and the Lewis acid material. The Lewis acid material preferably is a silver salt. In a particularly preferred embodiment, a thermographic image-recording material for producing dye images is provided which comprises a support carrying a dior triarylmethane thiolactone, dithiolactone or thioether dye precursor, an organic silver salt and optionally, a heat-fusible organic acidic material. For photothermographic use, the image-recording material additionally includes in catalytic association with the organic silver salt, a photosensitive silver halide or a photosensitive silver halide-forming component and a reducing agent. Preferably, the dye precursor is a triarylmethane thiolactone, particularly, a thiophthalide and the organic silver salt is silver behenate.

Novel imaging systems useful for light-sensitive, heat-sensitive, pressure-sensitive and other image-recording materials for producing dye images and particularly imaging systems which employ the subject di- and triarylmethane dye precursors and an organic silver salt are disclosed and claimed in copending U.S. patent application Ser. No. 935,534 of E. J. Dombrowski, J. R. Freedman and P. F. King filed concurrently herewith, which is a continuation-in-part of application Ser. No. 809,157 filed Dec. 16, 1985 (now abandoned).

The novel di- and triarylmethane dye precursors of the present invention may be represented by the formula

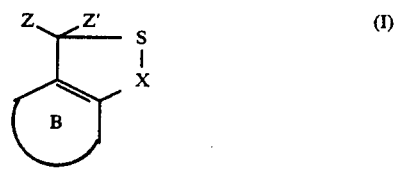

wherein X is

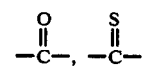

or $-CH_2-$; ring B represents a substituted or unsubstituted carbocyclic aryl ring, e.g., of the benzene or naphthalene series or a heterocyclic aryl ring, e.g., pyridine or pyrimidine; and Z and Z' taken individually represent the moieties, to complete the auxochromophoric system of a diarylmethane or a triarylmethane dye when said S-containing ring is open and Z and Z' when taken together represent the bridged moieties to complete the auxochromophoric system of a bridged triarylmethane dye when said S-containing ring is open. In a preferred embodiment, B represents a substituted or unsubstituted benzene ring and Z and Z' taken individually represent the aryl moieties, the same or different, to complete the auxochromophoric system of a triarylmethane dye when said S-containing ring is open and Z and Z' when taken together represent the bridged aryl moieties to complete the auxochromophoric system of a briged triarylmethane dye when said S-containing ring is open. Usually, at least one of Z and Z' whether taken individually or together possesses as an auxochromic substituent, a nitrogen, oxygen or sulfur atom or a group of atoms containing nitrogen, oxygen or sulfur. Preferably, X is

In the triarylmethane compounds represented in formula I above, the aryl moieties Z and Z', when taken individually, may be the same or different and typically represent heterocyclic aryl groups containing nitrogen, oxygen or sulfur as the heterocyclic atom, particularly N-heterocyclic aryl groups such as julolidin-3-yl, indol-3-yl, pyrr-2-yl, carbazol-3-yl, and indolin-5-yl wherein the N atom of the indolyl, pyrryl, carbazolyl and indolinyl groups may be substituted with hydrogen or alkyl having 1 to 6 carbon atoms, or the aryl moieties Z and Z' typically may be carbocyclic aryl, particularly phenyl or naphthyl groups which include an appropriately positioned auxochromic substituent, i.e., an atom or group that produces an auxochromic effect, which substituent is usually positioned para to the meso carbon atom. Typically, Z and Z' when taken together represent aryl groups bridged by a heteroatom, such as, oxygen, sulfur or nitrogen to form, for example, 4H-chromeno [2,3-C] pyrazole and particularly represent carbocyclic aryl groups, such as, phenyl groups bridged with a heteroatom, preferably oxygen, sulfur or nitrogen substituted with hydrogen or an alkyl group having 1 to 6 carbon atoms to provide a xanthene, thioxanthene or an acridine dye, which dyes possess an auxochromic substituent(s) para to the meso carbon atom, i.e., in the 3-position or in the 3,6-positions or meta and para to the meso carbon atom, i.e., in the 3,7-positions.

In the diarylmethane compounds, one of Z and Z' may be heterocyclic aryl or carbocyclic aryl as discussed above and the other of Z and Z' may be, for example, phenoxy, thiophenoxy, alkoxy containing 1 to 20 carbon atoms, alkylthio containing 1 to 20 carbon atoms, -N,N-(disubstituted)amino wherein each said substituent may be alkyl containing 1 to 20 carbon atoms, carbocyclic aryl containing 6 to 12 carbon atoms, aralkyl containing 7 to 15 carbon atoms particularly phenyl- and naphthyl-substituted alkyl or alkaryl containing 7 to 15 carbon atoms particularly alkyl-substituted phenyl and naphthyl. Representative alkyl groups include methyl, butyl, hexyl and octadecyl and representative aryl groups include phenyl and naphthyl. Representative alkaryl groups include p-octylphenyl, o-methylnaphthyl and p-hexylphenyl, and representative aralkyl groups include phenethyl, benzyl and naphthylmethyl.

Examples of useful auxochromic substituents include —OR$_1$ wherein R$_1$ is hydrogen, alkyl usually having 1 to 6 carbon atoms, aralkyl usually having 7 to 15 carbon atoms, alkaryl usually having 7 to 15 carbon atoms or carbocyclic aryl usually having 6 to 12 carbon atoms; —SR$_2$ wherein R$_2$ has the same meaning given for R$_1$; —NR$_3$R$_4$ wherein R$_3$ and R$_4$ each represent hydrogen, alkyl usually having 1 to 6 carbon atoms, $\beta$-substituted ethyl, cycloakyl usually having 5 to 7 carbon atoms, aralkyl usually having 7 to 15 carbon atoms, alkaryl usually having 7 to 15 carbon atoms or

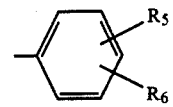

wherein R$_5$ and R$_6$ each are hydrogen, alkyl usually having 1 to 6 carbon atoms, halo such as chloro, bromo, fluoro, and iodo, nitro, cyano, alkoxycarbonyl wherein said alkoxy has 1 to 6 carbon atoms, sulfonamido (—NHSO$_2$R$_0$), sulfamoyl (—SO$_2$NHR$_0$), sulfonyl (—SO$_2$R$_0$), acyl (—COR$_0$) or carbamyl (—CONR$_0$) wherein R$_0$ usually is alkyl having 1 to 20 carbon atoms, benzyl or phenyl and R$_3$ and R$_4$ taken together represent the atoms necessary to complete a heterocyclic ring usually piperidino, pyrrolidino, N-methylpiperidino, morpholino or

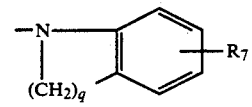

wherein q is an integer 2 to 5 and R$_7$ has the same meaning as R$_5$,

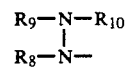

wherein R$_8$ and R$_9$ each are hydrogen, alkyl usually having 1 to 6 carbon atoms or

wherein R$_{11}$ and R$_{12}$ have the same meaning as R$_5$ and R$_6$ and R$_{10}$ is —COR$_{13}$, —CSR$_{13}$ or —SO$_2$R$_{13}$ wherein R$_{13}$ is hydrogen, alkyl usually having 1 to 6 carbon atoms, phenyl, —NH$_2$, —NHR$_{14}$, —N(R$_{14}$)$_2$ or —OR$_{14}$ wherein R$_{14}$ is hydrogen, alkyl usually containing 1 to 6 carbon atoms or phenyl. Representative alkyl groups include methyl, ethyl, propyl, butyl and hexyl. Representative $\beta$-substituted ethyl groups include $\beta$-methoxymethoxyethyl and $\beta$-2'-tetrahydropyranyloxyethyl. Representative aralkyl groups include phenyl and naphthyl-substituted alkyl, such as, benzyl, phenethyl and naphthylmethyl and representative alkaryl groups include alkyl-substituted phenyl and naphthyl, such as, o-methylphenyl, o-methylnaphthyl and p-hexylphenyl. Representative carbocyclic aryl groups include phenyl and naphthyl and representative cycloalkyl groups include cyclopentyl, cyclohexyl and cycloheptyl. It will be appreciated that the auxochromic substituent(s) will be selected for a given diarylmethane, triarylmethane or bridged triarylmethane compound to provide the desired chromophore color upon opening of the S-containing ring and to achieve facile color formation.

In addition to the auxochromic substituents, the subject dye precursor compounds may possess one or more additional substituents on Z and/or Z' and/or ring B as may be desired that do not interfere with the intended utility for the dye. Typical substituents include carboxy; hydroxy; cyano; thiocyano; mercapto; sulfo; nitro; sulfonamido (—NHSO$_2$R$_0$); sulfamoyl (—SO$_2$NHR$_0$); sulfonyl (—SO$_2$R$_0$); acyl (—COR$_0$); carbamyl (—CONR$_0$); halomethyl such as trifluoromethyl; alkyl usually having 1 to 20 carbon atoms such as methyl, octyl, hexadecyl; alkoxy usually having 1 to 20 carbon atoms such as methoxy, ethoxy, propoxy and butoxy; alkoxycarbonyl having 1 to 20 carbon atoms such as ethoxy- and dodecyloxycarbonyl; aralkyl usually having 7 to 15 carbon atoms, for example, phenyl- or naphthyl-substituted aklyl such as benzyl, phenethyl and naphthylmethyl; alkaryl usually having 7 to 15 carbon atoms, for example, alkyl substituted phenyl or naphthyl such as o-methylphenyl, o-methylnaphthyl and p-hexylphenyl; aralkyloxy usually having 7 to 15 carbon atoms, for example, phenyl- or naphthyl-substituted alkoxy such as benzyloxy, phenethyloxy and naphthylmethyloxy; aryloxy usually containing 6 to 12 carbon atoms such as phenoxy and naphthoxy; thioalkyl groups, usually having 1 to 20 carbon atoms such as methylthio, ethylthio and hexylthio; thioaryl and thioaralkyl groups containing up to 15 carbon atoms such as phenylthio, naphthylthio, benzylthio halo such as chloro, bromo, fluoro and iodo; amino including mono- and disubstituted amino such as —NR$_{15}$R$_{16}$ wherein R$_{15}$ and R$_{16}$ each are hydrogen, alkyl usually having 1 to 20 carbon atoms, aralkyl usually having 7 to 15 carbon atoms and aryl having 6 to 12 carbon atoms; and a fused substituent such as a fused benzene ring.

The dye precursor compounds of the present invention can be monomeric or polymeric compounds. Suitable polymeric compounds are those which, for example, comprise a polymeric backbone chain having dye precursor moieties attached directly thereto or through pendant linking groups. Polymeric compounds of the invention can be provided by attachment of the dye precursor moiety to the polymeric chain via the Z and/or Z' moieties or the ring B. For example, a monomeric dye precursor compound having a reactable substituent group, such as an hydroxyl or amino group, can be conveniently reacted with a mono-ethylenically unsaturated and polymerizable compound having a functional and derivatizable moiety, to provide a polymerizable monomer having a pendant dye precursor moiety. Suitable mono-ethylenically unsaturated compounds for this purpose include acrylyl chloride, methacrylyl chloride, methacrylic anhydride, 2-isocyanatoethyl methacrylate and 2-hydroxyethyl acrylate, which can be reacted with an appropriately substituted dye precursor compound for production of a polymerizable monomer which in turn can be polymerized in known manner to provide a polymer having the dye precursor compound pendant from the backbone chain thereof.

In this manner, a dye precursor compound having the structure illustrated in Example 15 hereof can be reacted with 2-isocyanatoethyl methacrylate for production of the corresponding urethane derivative via reaction of the respective hydroxyl and isocyanate groups. The desired polymer can then be obtained by free-radical initiated addition polymerization, using a free-radical catalyst such as α,α'-azodiisobutyronitrile (AIBN) according to known methodology. It will be appreciated, however, that other dye precursor compounds can be attached via other means to other polymerizable compounds for the production of other polymeric compounds having the desired property of forming color with Lewis acids, particularly heavy metal ions as discussed above.

Preferred compounds of the present invention are those represented by the formula

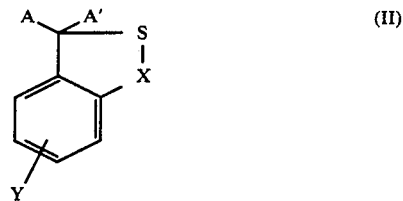

wherein X is

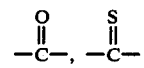

or —CH$_2$—; Y is hydrogen, alkyl having 1 to 6 carbon atoms, having 1 to 6 carbon atoms, alkoxycarbonyl having 1 to 6 carbon atoms, carboxy, cyano, thiocyano, nitro, sulfo, sulfonamido, sulfamoyl, sulfonyl, acyl, carbamyl, halo, —OR wherein R is hydrogen, alkyl having 1 to 6 carbon atoms, benzyl or phenyl, —SR$^0$ wherein R$^0$ has the same meaning as R or —NR$^5$R$^6$ wherein R$^5$ and R$^6$ each are hydrogen, alkyl having 1 to 6 carbon atoms, β-substituted ethyl, benzyl or phenyl; A and A', the same or different, are selected from phenyl substituted in the 4-position with —OR$^1$ wherein R$^1$ has the same meaning as R, —SR$^2$ wherein R$^2$ has the same meaning as R or —NR$^5$R$^6$ wherein R$^5$ and R$^6$ have the same meaning given above and substituted in the 2-, 3-, 5- and 6-positions with hydrogen, alkyl having 1 to 6 carbon atoms, alkoxy having 1 to 6 carbon atoms or chloro or substituted in the 5- and 6-positions with a fused benzene ring; indol-3-yl substituted in the 1 and 2 positions with hydrogen, alkyl having 1 to 6 carbon atoms, benzyl or phenyl; pyrr-2-yl substituted in the 1-position with hydrogen, alkyl having 1 to 6 carbon atoms, benzyl or phenyl; and carbazol-3-yl substituted in the 9-position with hydrogen, alkyl having 1 to 6 carbon atoms, benzyl or phenyl and A and A' taken together represent phenyl groups bridged by a heteroatom selected from oxygen, sulfur and nitrogen substituted with hydrogen or alkyl having 1 to 6 carbon atoms to form xanthene, thioxanthene or acridine (a) substituted in the 3- and 6-positions with a group, the same or different, selected from —OR$^3$ wherein R$^3$ has the same meaning as R, —SR$^4$ wherein R$^4$ has the same meaning as R and —NR$^7$R$^8$ wherein R$^7$ is hydrogen or alkyl having 1 to 6 carbon atoms and R$^8$ is alkyl having 1 to 6 carbon atoms, benzyl or

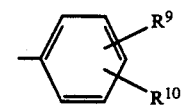

wherein R$^9$ and R$^{10}$ each are hydrogen, alkyl usually having 1 to 6 carbon atoms, alkoxy having 1 to 6 carbon atoms, chloro, nitro, cyano, alkoxycarbonyl wherein said alkoxy has 1 to 6 carbon atoms, sulfonamido, sulfamoyl, sulfonyl, acyl, or carbamyl and R$^9$ and R$^{10}$ taken together represent indolino, indolino substituted with acyl or

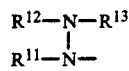

wherein $R^{11}$ and $R^{12}$ each are hydrogen, alkyl having 1 to pb 6 carbon atoms or

wherein $R^{14}$ and $R^{15}$ have the same meaning as $R^9$ and $R^{10}$ and $R^{13}$ is —$COR^{16}$ wherein $R^{16}$ is hydrogen, alkyl having 1 to 6 carbon atoms or phenyl and substituted in the 1-, 2-, 4-, 5-, 7- and 8-positions with hydrogen, alkyl having 1 to 6 carbon atoms, alkoxy having 1 to 6 carbon atoms or chloro or (b) substituted in the 3-position with —$NR^{17}R^{18}$ wherein $R^{17}$ is hydrogen, alkyl having 1 to 6 carbon atoms, cycloalkyl having 5 to 7 carbon atoms, benzyl or phenyl and $R^{18}$ is alkyl having 1 to 6 carbon atoms, cycloalkyl having 5 to 7 carbon atoms, benzyl or phenyl and $R^{17}$ and $R^{18}$ taken together represent piperidino, pyrrolidino, N-methylpiperidino or indolino and (1) substituted in the 7- and 8-positions with a fused benzene ring or (2) substituted in the 7-position with hydrogen, —$NR^{17}R^{18}$ wherein $R^{17}$ and $R^{18}$ have the same meaning given above, alkyl having 1 to 6 carbon atoms, alkoxy having 1 to 6 carbon atoms or chloro and substituted in the 1-, 2-, 4-, 5-, 6- and 8-positions with hydrogen, alkyl having 1 to 6 carbon atoms, alkoxy having 1 to 6 carbon atoms or chloro. Preferably, X is

The di- and triarylmethane thiolactone dye precursors of the foregoing formulae can be synthesized from the corresponding lactones by heating substantially equimolar amounts of the lactone and phosphorus pentasulfide to reflux in pyridine or other suitable solvent or by heating with phosphorus heptasulfide in tetrahydrofuran or other solvent. Under these conditions, the thiolactone together with the dithiolactone are obtained as the two major products of the reaction which are then recovered from the reaction mixture, for example, by precipitation and then isolated using conventional techniques such as column chromatography. If desired, the dithiolactone may be converted to the thiolactone by oxidation using, for example, hydrogen peroxide. Conversely, the thiolactone may be converted to the dithiolactone by further reaction with phosphorus pentasulfide.

It is quite surprising that the subject thiolactones, particularly, the thiophthalide dye precursors can be synthesized directly from the corresponding phthalides using phosphorus pentasulfide or its equivalent, since the products obtained by reacting fluorane, fluoresceinchloride and diphenylphthalide with phosphorus pentasulfide gave only the corresponding dithiophthalides as reported by R. Meyer, ibid. and I. P. Soloveichik, et al., ibid. It is believed that the unexpected formation of thiophthalide in admixture with dithiophthalide is due to the electronic effects of an auxochromophoric system in the starting phthalide which is absent in the starting materials used previously. Presumably, the auxochromic function through resonance and inductance stabilizes the incipient carbonium ion forming the charge center of the open dye form to impart special reactivity to the starting phthalide. In this regard, it is well known that the leuco-phthalide dye-formers used as starting materials can be readily converted to their conjugate dye-acid form as illustrated below in scheme (i). Fluorane, fluoresceinchloride and diphenylphthalide are not comparably sensitive.

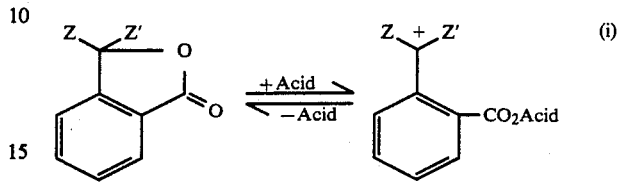

wherein Z and Z' have the same meaning given above.

Presumably, this property of the leuco-phthalide starting materials also provides the basis for the preferred new synthesis of the subject dye precursors of the thiolactone type. According to this new method, di- and triarylmethane thiophthalide dye precursors, for example, can be obtained substantially free of dithiophthalide via "an activating intermediate complex" which is "trapped" with sulfide by reaction with, for example, $NaHS \cdot XH_2O$, $Na_2S$ or $H_2S$ to yield the corresponding thiophthalide as illustrated below.

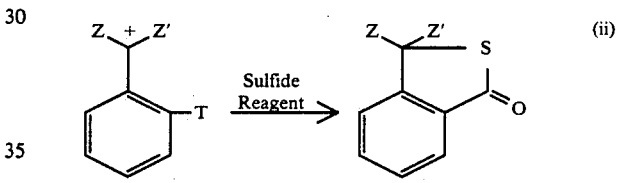

wherein T is preferably —COCl or

wherein E is alkyl having 1 to 4 carbon atoms or benzyl and Z and Z' have the same meaning given above.

The leuco-phthalide starting material can be converted to the corresponding dye-acid chloride or dye-ester intermediate in a known manner. For example, Stadler, Paul Albert, Helvitica Chimica Acta, Vol. 61, Fasc. 5 (1978), No. 162, p. 1675, reports the reaction of oxalylchloride with dimethylformamide in a suitable solvent to give dimethylformamide imide chloride followed by the addition of an acid to this suspension to furnish an activated carboxy-group derivative. The activated carboxy-group derivative is then transformed to an ester by addition of pyridine and an alcohol or phenol. Chandrasekaran, S. and John V. Turner, Synthetic Communications, 12(9), pp. 727–731 (1982) describe carboxy group activation at $-30°$ to $-20°$ C. using methane sulfonyl chloride and triethylamine and then treating the intermediate mixed anhydride in situ with an alcohol to give the ester. It is noted that dimethyl aminopyridine catalysis may be used to enhance esterification rates. Also, the authors note that the procedure can be used to prepare thiol esters or amides.

In the subject method, the leuco-phthalide starting material is reacted with a slight excess, usually a 0.2 to 0.3 molar excess of an acid chloride such as thionyl or oxalyl chloride in a suitable organic solvent. The solvent employed can be readily selected for the given reactants. Typical solvents include methylene chloride, acetonitrile and pyridine. When thionylchloride is employed, dimethylaminopyridine may be used to catalyze the reaction. The reaction temperature usually varies between about −20° and 20° C.

The —COCl intermediate thus formed is then reacted with a sulfide reagent, such as, hydrogen sulfide, sodium sulfide or sodium hydrogen sulfide or its hydrate. The sulfide reagent may be added to the reaction solution containing the intermediate or the solution containing the intermediate may be added to a solution of the sulfide reagent dissolved in a suitable solvent. Preferably, the reaction solution of activated intermediate is quenched into a methanol solution of sodium hydrogen sulfide hydrate. The temperature for the reaction between the intermediate and sulfide reagent usually varies between about −20° and 20° C. If desired, the —COCl intermediate can be isolated before the reaction with the sulfide reagent, and if desired, the —COCl intermediate can be converted to the corresponding ester by reaction with an alkanol or benzyl alcohol prior to reaction with the sulfide reagent. Also, the starting lactone can be converted directly to the ester by acid esterification using an acidified alcohol, for example, by refluxing the lactone in benzyl alcohol or a 1–4 carbon alkanol acidified with a mineral acid and the $$-\overset{\overset{\displaystyle O}{\|}}{C}OE$$

intermediate reacted with the sulfide reagent as above.

The above reactions to form a thiophthalide or other thiolactone dye precursor are not usual or general to all lactones, such as, simple lactones and non-dye forming phthalides. For example, it has been found that 2,2-disubstituted phthalide non-dye formers such as diphenylphthalide and fluoresceinchloride cannot be converted to their thiophthalides through an activating intermediate. Their lack of reactivity with oxalylchloride under the above described conditions presumably is due to the absence of an auxochromic function. As mentioned previously, it is believed that the property of the leuco-phthalide dye formers to be easily converted to their conjugate dye-acid forms the basis for this new synthesis. As to simple lactones, the synthetic route reported by Kaloustian, M. K. and F. Khouri, Tetrahedron Letters, Vol. 22, p. 413–416 (1981) shows that simple lactones undergo O-alkylation with Meerwein's salts to form an intermediate lactonium salt which when reacted with anhydrous sodium hydrosulfide in acetonitrile at 0° C. affords the corresponding thionolactone rather than thiolactones.

The thioether compounds may be synthesized, for example, by reducing both the lactone and the dye to the leuco form followed by halogenating the alcohol and reacting the latter compound with thiolpropionic acid, then oxidizing the leuco dye and treating with base to give the desired thioether product.

Starting materials useful in synthesizing the subject dye precursors are the corresponding lactones of the compounds defined in formulae I and II above. Lactone compounds are well known in the art and may be synthesized using various conventional methods. Indeed, numerous di- and triarylmethane dyes including bridged triarylmethanes possessing a lactone ring-closing moiety or capable of being derivatized with a lactone ring-closing moiety have been described in Venkataraman, K., The Chemistry of Synthetic Dyes, Academic Press, Inc., New York, 1952, pp. 705–760 and 1111 and in U.S. Pat. Nos. 3,491,111; 3,491,112; 3,491,116; 3,509,173; 3,509,174; 3,514,310; 3,514,311; 3,775,424; 3,853,869; 3,931,227; 3,959,571; 4,267,251; 4,535,172 4,341,403 and 4,535,348. If the lactone starting materials possess hydroxy, carboxy, mercapto or other substituents that may require blocking during synthesis, conventional protecting groups may be employed as described by McOmie, J. F. W., Protective Groups in Organic Chemistry, Plenum Press, New York, 1973 and by Greene, Theodora W., Protective Groups in Organic Synthesis, John Wiley & Sons, New York, 1981.

The following examples are given to further illustrate the present invention and are not intended to limit the scope thereof. It will be understood that the ring-closed thiolactone, dithiolactone and thioether compounds are substantially colorless and in their ring-opened form give the chromophore color indicated in the examples.

Also, it will be understood that in the following examples, Me Cell denotes 2-methoxyethanol, TMS denotes tetramethylsilane, $CDCl_3$ denotes deuterochloroform, MeOH denotes methanol, and that E represents the extinction coefficient at the wavelength indicated.

EXAMPLE 1

Preparation of the compounds having the formulae

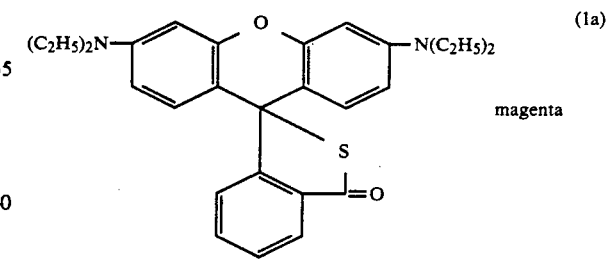

magenta

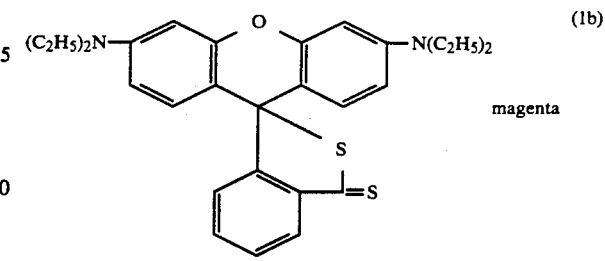

magenta

Rhodamine B (10 g; 0.02 mol) and phosphorus pentasulfide (4.6 g; 0.2 mol) were heated to reflux in pyridine (250 ml) for four hours. The cooled solution was quenched in 500 g ice—250 ml concentrated hydrochloric acid. The pH was adjusted to pH 5 with aqueous sodium hydroxide. The solid was collected and air dried. The crude was purified by chromatography (silica gel, methylene chloride) to yield two major products, 5 g of the thiolactone compound of formula 1a as a tan solid and 1.5 g of the dithiolactone compound of formula 1b as a red crystalline solid.

Compound 1a:

UV (Me Cell) $\lambda_{max}$ 237 nm (E=66,000) 282 nm (E=33,600) 319 nm (E=17,200). IR (KBr, cm$^{-1}$) 1675, 1608. NMR: (CDCl₃, TMS)δ 6.2–7.8 m (10H, m), 3.25 (8H, q), 1.1 (12H, t).

Anal. Calc. for C₂₈H₃₀N₂SO₂: C, 73.4; H, 6.5; N, 6.1; S, 7.0; O, 7.0. Found: C, 73.51; H, 6.76; N, 6.0; S, 6.87.

Compound 1b:

UV (Me Cell) λ$_{max}$ 240 nm (E=58, 400), 285 nm (E=35,200), 324 nm (E=30,000), 415 nm (E=1,600). IR (KBr, cm⁻¹) 1618.

Anal. Calc. for C₂₈H₃₀N₂S₂O: C, 70.1; H, 6.3; N, 5.9; S, 13.5; O, 3.4. Found: C, 70.6; H, 6.5; N, 5.8; S, 13.2

EXAMPLE 2

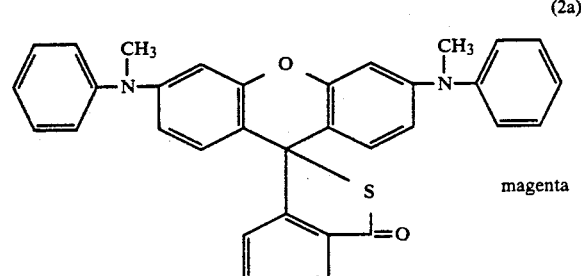
(2a) magenta and

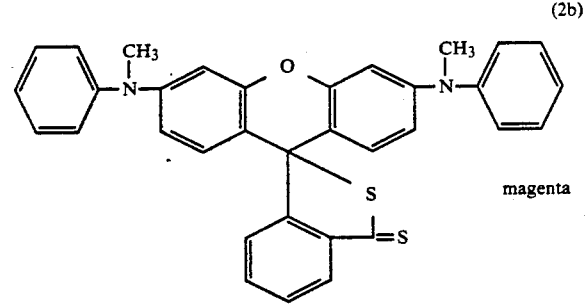
(2b) magenta

The title compounds were prepared from the corresponding phthalide following the procedure given in Example 1.

Compound 2a:

UV (Me Cell) λ$_{max}$ 238 nm (E=52,200), 303 nm (E=26,800). IR (KBr, cm⁻¹) 1682, 1598. NMR (CDCl₃, TMS)δ 6.2–7.7 (30H, m), 3.2 (6H, s).

Anal. Calc. for C₃₄H₂₆N₂O₂S: C, 77.6; H, 4.9; N, 5.3; S, 6.08. Found: C, 77.89; H, 5.13; N, 5.19; S. 5.89.

Compound 2b:

UV (Me Cell) λ$_{max}$ 238 nm (E=50,000), 306 nm (E=31,600), 415 nm (E=1000). IR (KBr cm⁻¹) 1590. M/e 452.

EXAMPLES 3–11

The following thiophthalides were prepared from the corresponding phthalide following the procedure given in Example 1.

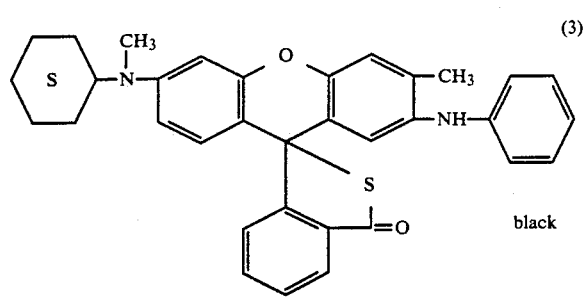
(3) black

UV (Me Cell) λ$_{max}$ 236 nm (E=37,600), 281 nm (E=35,200), 315 nm (E=15,200).

IR (KBr, cm⁻¹) 1680, 1603.

NMR (CDCl₃, TMS)δ 6.2–7.9 (14H, m), 5.15 (1H, s), 3.5 (1H, s), 2.7 (3H, s), 2.15 (3H, s), 0.9–1.9 (11H, m). M/e 532.7

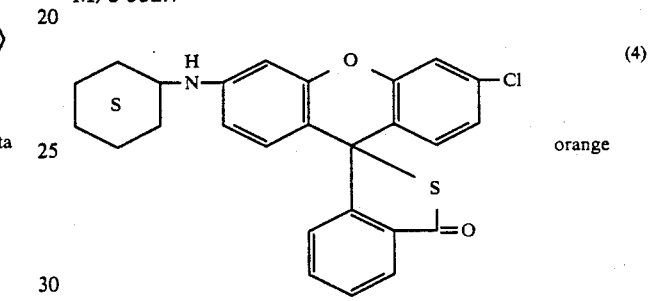
(4) orange

IR (KBr, cm⁻¹) 1690, 1630, 1600.

UV (Me Cell) λ$_{max}$ 233 nm (E=43,200), 282 nm (E=17,600), 315 nm (E=6,600).

VIS (MeOH, 10 mg AgNO₃) λ$_{max}$ 450 nm (E=24,000), 474 nm
(E=33,200), 500 nm (E=27,200).
M/e 448.

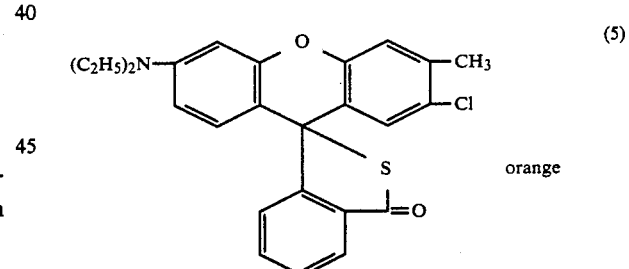
(5) orange

NMR (CDCl₃, TMS)δ 6.2–8.0 (m, 9H), 3.3 (q, J=3 Hz, 4H) 2.3 (2,3H), 1.2 (t, J=3 Hz, 6H).

IR (KBr, cm⁻¹) 1692, 1637, 1618.

UV (Me Cell) λ$_{max}$ 236 nm (E=40,000), 285 nm (E=16,800), 325 nm, (E=7,300).

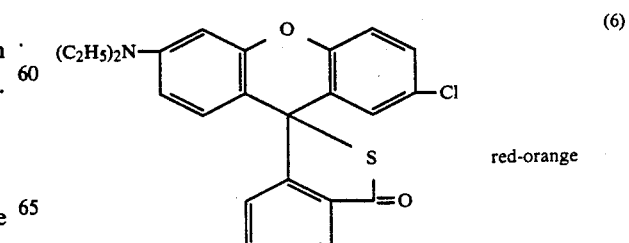
(6) red-orange

NMR (CDCl₃, TMS)δ 6,8–8.0 (m, 10H), 3.3 (q, J=3Hz, 9H), 1.15 (t, J≈3 Hz, 6H).

IR (KBr, cm⁻¹) 1680, 1630.

UV (Me Cell) $\lambda_{max}$ 237 nm (E=37,400), 281 nm (E=18,800), 325 nm (E=6,900).

Vis (MeOH, 10 mg AgNO₃) $\lambda_{max}$ 480 nm (E=23,600), 497 nm (E=29,600), 530 nm (E=23,200).

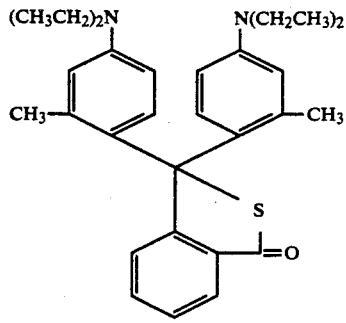

(7) green

NMR (CDCl₃, TMS)δ 6.3–8.0 (m, 10H), 3.3 (q, J≈3H, 8H), 2.2 (s, 3H), 1.95 (s, 3H), 1.15 (t, J=3 Hz, 12H).

IR (CH₂Cl₂, cm⁻¹) 1674, 1605.

Anal. Calc. for C₂₈H₃₆N₂OS: C, 74.96; H, 8.09; N, 6.20; S, 7.15.

Found: C. 74.83; H, 7.56; N, 5.78; S, 6.91.

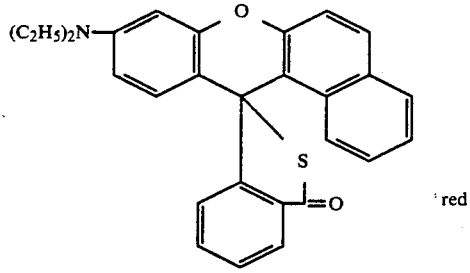

(8) red

NMR (CDCl₃ TMS)δ 6.3–8.2 (m, 13H), 3.4 (q, J≈3 Hz, 4H), 1.20 (t, J≈3 Hz, 6H).

IR (KBr, cm⁻¹) 1678, 1627.

UV (Me Cell) $\lambda_{max}$ 252 nm (E=58,800), 283 nm (E=25,800), 325 nm (E=6,600).

VIS (MeOH, 10 mg AgNO₃) $\lambda_{max}$ 490 nm (E=26,400), 520 nm (E=40,000), 554 nm (E=36,400).

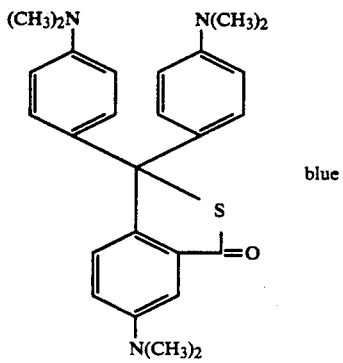

(9) blue

VIS (MeOH, 10 mg, AgNO₃) $\lambda_{max}$ 604 nm (E=57,600).

UV (Me Cell) $\lambda_{max}$ 275 nm (E=50,000), 380 nm (E=2,200).

IR (KBr, cm⁻¹) 1678, 1618.

M/e 431.6

Anal. Calc. for C₂₆H₂₉N₃OS: C, 72.36; H, 6.77; N, 9.71; S, 7.43. Found: C, 72.24; H, 6.33; N, 9.48; S. 7.69.

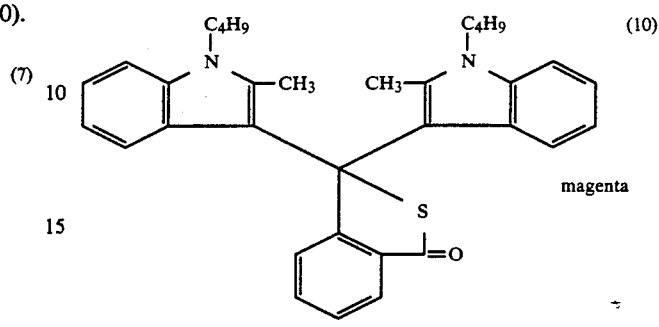

(10) magenta

VIS (MeOH, 10 mg AgNO₃) $\lambda_{max}$ 535 nm (E=34,400).

UV (Me Cell) $\lambda_{max}$ 284 nm (E=18,800).

IR (KBr, cm⁻¹) 1678.

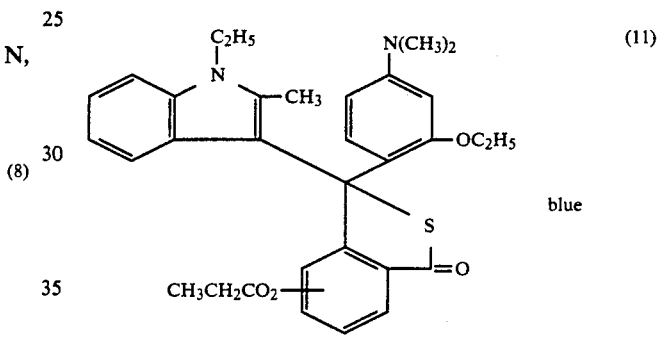

(11) blue

IR (KBr, cm⁻¹) 1720, 1670, 1605.

UV (MeOH) $\lambda_{max}$ 225 nm (E=22,400), 275 nm (E=28,000).

VIS (MeOH), 10 mg AgNO₃) $\lambda_{max}$ 583 nm (E=50,000).

As in Examples 1 and 2 above, the dithiophthalides corresponding to the thiophthalides of Examples 3 to 11 also were obtained. Typically, the thiophthalides are recovered as colorless or lightly colored solids and the dithiophthalides as reddish solids.

EXAMPLE 12

Preparation of the compound having the formula

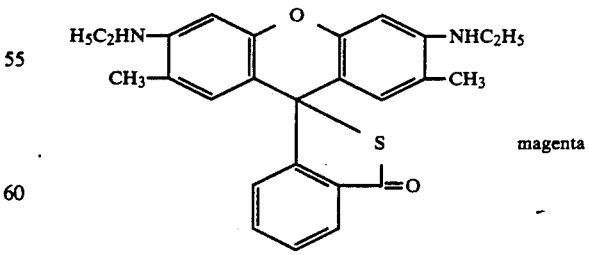

magenta

To Rhodamine 6G (0.5 g, 0.001 mol) in a solution of acetone (20 ml) and water (5 ml) at a temperature between room temperature and −10° C. was added sodium hydrosulfide hydrate dropwise initially, then 1 ml at a time. The mixture was kept at −10° C. for 1.5 hours during which time a pink precipitate formed. The mixture was allowed to warm to room temperature to determine if it would affect precipitate formation. The mixture was refrigerated overnight. Impurities that coprecipitated with the product were removed by washing with hot methanol. The solution was filtered (hot) under suction and the title compound recovered as a pink solid was dried under vacuum (50° C.). The compound was identified by NMR (CDCl$_3$—D$_2$O) and by UV (MeOH, AgNO$_3$-10%).

The Rhodamine 6G used as the starting material in the foregoing example has the formula

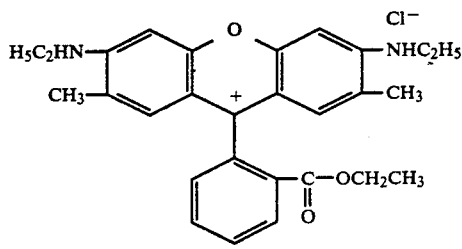

EXAMPLE 13

Preparation of the compound having the formula

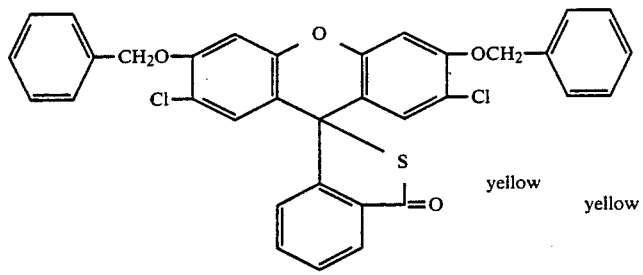

To 2,7-diochlorofluorescein (2.0 g, 0.005 mol) in acetone (30 ml) was added potassium carbonate (4.1 g, 0.0296 mol). While stirring, α-bromotoluene (1.9 ml, 0.0111 mol) was added dropwise and the solution was allowed to reflux for 2.5 hours, during which time the unidentified pinkish solid was generated. One equivalent of α-bromotoluene was added after 3.5 hours. The solution was stirred continuously for 18 hours and then filtered to give the alkylated ester intermediate of the formula

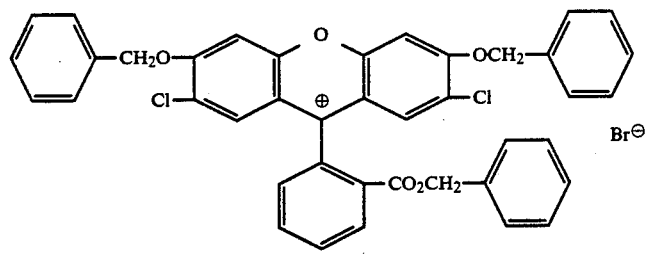

A concentrated solution of sodium hydrogen sulfide hydrate (3 g. in 7 ml water) was added dropwise to a solution of the alkylated ester intermediate in 50 ml acetone at room temperature. After 1.5 hours additional sodium hydrogen sulfide hydrate was added (6 g. in 10 ml water). Several grams of dry NaSH was then added and the mixture was stirred for another hour. A moderate volume of ethyl acetate and saturated aqueous sodium chloride solution was added. The ethyl acetate layer was extracted with distilled water and dried over sodium sulfate. The organic layer was then evaporated to give the crude title compound as a yellow-orange solid which was dried under vacuum.

EXAMPLE 14

Preparation of the compound having the formula

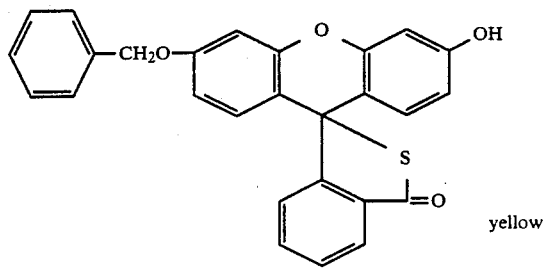

The title compound was prepared in the same manner described in Example 13 by alkylating fluorescein with α-bromotoluene to give the ester intermediate of the formula

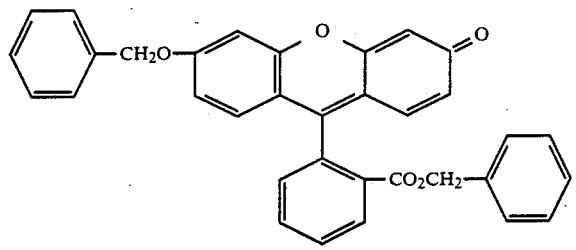

followed by reacting the intermediate with NaHS in methanol solution.

EXAMPLE 15

Preparation of the compound having the formula

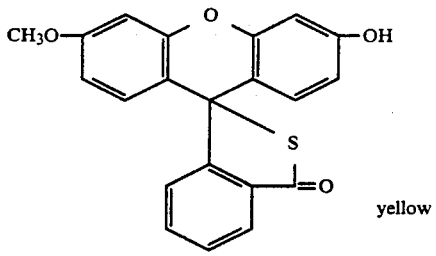

yellow

The title compound was prepared in the same manner described in Example 13 by alkylating fluorescein with methyltosylate to give the ester intermediate of the formula

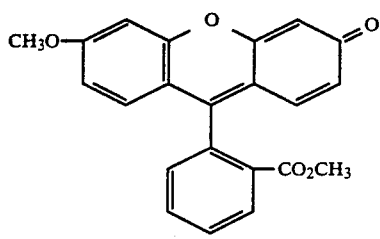

followed by reacting the intermediate with NaHS in methanol solution.

Using the following procedure, the title compound was derivatized to give a polymerizable monomeric compound having the formula

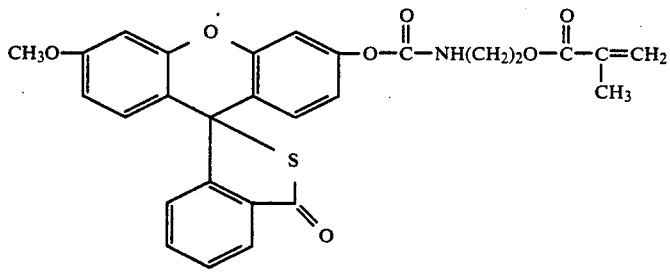

The compound of Example 15 (1.74 g, 4.81 mmol) was placed in a 100 ml round bottom flask and dissolved upon reflux in methylene chloride (60 ml). Isocyanatoethyl methacrylate (7.2 mmol, 1.02 ml) and a catalytic amount of dibutyltin diacetate was added to the refluxing solution. A quantitative yield of the crude product was obtained. Purification was accomplished by reducing the volume of the reaction mixture in vacuo. The reaction concentrate was applied onto a packed column of silica gel and eluted with methylene chloride. The complete removal of solvent from the recovered elutent in vaco yielded the monomeric compound as a light yellow solid. Yield 2.03 g (82% by weight).

EXAMPLE 16

Preparation of the compound having the formula

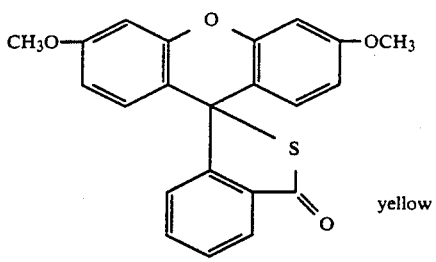

yellow

The title compound was prepared by reacting one equivalent of the compound prepared in Example 15 with about four equivalents of dimethylsulfate at reflux in acetone solution containing five equivalents of potassium carbonate.

EXAMPLE 17

Preparation of the compound having the formula

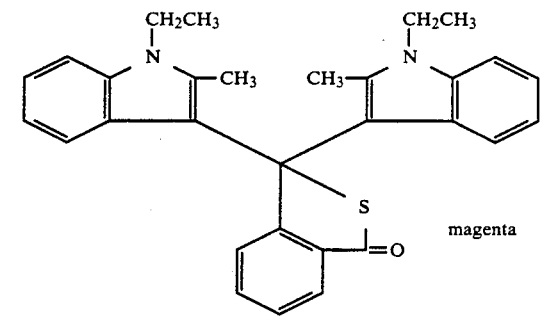

magenta

To a solution of 1 gram of 3,3-bis (1-ethyl-2-methylindol-3-yl) phthalide in 50 ml of methylene chloride was added 1 gram of oxalylchloride dropwise. Gas evolved immediately and a magenta solution was formed. After 2 hours, the solution was quenched in a solution of sodium hydrogen sulfide hydrate (2 grams) in methanol (30 ml). The magenta color was dispersed on mixing and a yellow solution resulted. The methylene chloride solution was washed with water, brine and dried over calcium sulfate. Solvent removal gave 1.2 grams of a crude yellow solid which was purified by silica chromatography to yield pure title compound.

EXAMPLE 18

The thiophthalide compound of Example 9 also was prepared as follows:

(a) A three-liter three-neck round bottom flash equipped with an overhead stirrer, nitrogen inlet and thermometer was charged with dimethylaminopyridine (70 g., 0.57 mol) and reagent grade acetonitrile (2 liters). The solution was cooled to an internal temperature of −20° C. at which point some minor crystallization of the pyridine occurred. Thionylchloride was added dropwise (69 g, 0.58 mol) over 20 minutes via addition funnel at a reaction temperature of −20° C. A white dispersion formed. The reaction was stirred at −20° C. for 15 minutes. Solid Crystal Violet Lactone (200 g, 0.48 mol) was added to the reaction at which point the dispersion turned blue. The reaction mixture was allowed to warm to 0° C. over 20 minutes and maintained at 0° C. for 2 hours.

(b) The blue solution was then added to a 0° C. solution of sodium hydrogen sulfide (200 g) in methanol (2 liters). The tan dispersion was diluted with water (4 liters) and then filtered. The solid was washed with water (2×4 liters) and dried. The crude was purified by high pressure liquid chromatography to yield 150 g of pure title compound as a light yellow solid.

In a further preparation, step (a) was repeated and then gaseous hydrogen sulfide was passed through the blue solution of acid chloride intermediate for one hour. The solution was further treated with gaseous hydrogen sulfide for 12 hours. The solid that formed was collected by filtration, and the crude material was purified by high pressure liquid chromatography to give 50% overall yield of pure title compound on a 10 gram scale.

Rather than adding the Crystal Violet Lactone to the thionyl chloride, step (a) was carried out by dissolving 0.25 mol of Crystal Violet Lactone in 250 ml of methylene chloride at room temperature, cooling the solution to 0° C. under nitrogen and then adding 0.26 mol of thionyl chloride at a rate to maintain the reaction temperature between 0° and 5° C. The reaction mixture became dark blue and after stirring under nitrogen at 0°-5° C. for two hours, the solution was added to a solution of sodium hydrogen sulfide in 250 ml methanol at a rate to maintain the temperature of the sodium hydrogen sulfide solution below 5° C.

EXAMPLE 19

The thiophthalide compound of Example 7 was prepared from the corresponding phthalide according to the procedure of steps (a) and (b) given in Example 18 above and yielded 35 g of pure compound on a 50 g scale.

EXAMPLE 20

The thiophthalide compound of Example 10 was prepared from the corresponding phthalide according to the procedure of steps (a) and (b) given in Example 18 above except methylene chloride was used as the solvent instead of acetonitrile in step (a) and the phthalide starting material was added as a methylene chloride solution. Pure title compound was obtained in 92% yield by extraction rather than chromatography.

EXAMPLE 21

Preparation of the compound having the formula

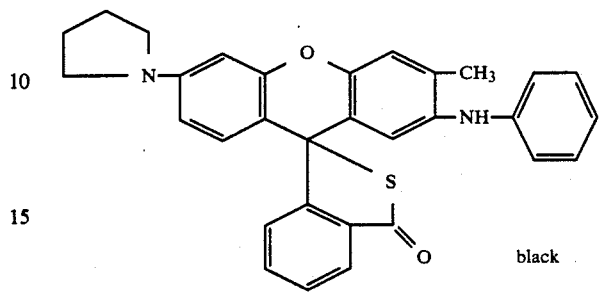

black

The title compound was prepared from the corresponding phthalide using the same procedure described in Example 18 above except methylene chloride was used as the solvent instead of acetonitrile in step (a).

EXAMPLE 22

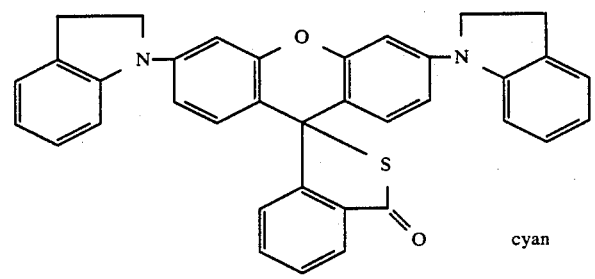

cyan

The title compound was prepared from the corresponding phthalide according to the procedure given in Example 17 above.

EXAMPLE 23

Preparation of the compound having the formula

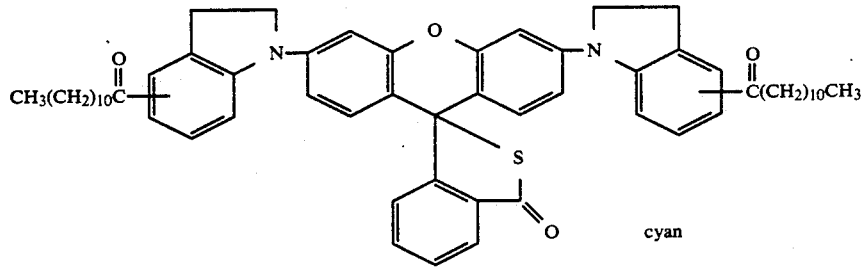

cyan

The title compound was prepared by reacting one equivalent of the compound prepared in Example 22 with 2.1 equivalents of lauryl chloride in methylene chloride solution containing 2.0 equivalents of stannic chloride.

EXAMPLE 24

The thiophthalide of Example 3 also was prepared by refluxing the starting phthalide in methanol (or n-butanol) acidified with sulfuric acid to give the corresponding ester having the formula

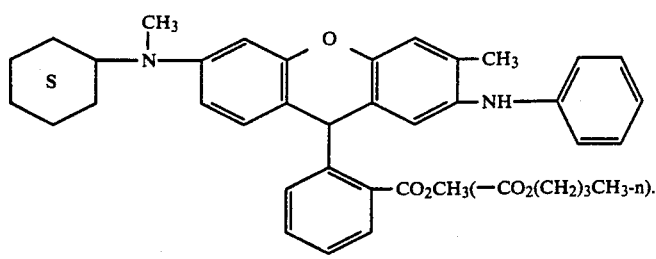

The reaction solution containing the ester intermediate was then added to a solution of sodium hydrogen sulfide in methanol at room temperature to give the corresponding thiophthalide.

EXAMPLE 25

Preparation of the compound having the formula

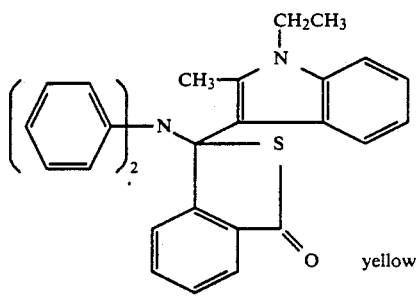

Oxalyl chloride (1.5., 0.012 mol) was added dropwise to a solution of the following phthalide (5 g., 0.011 mol) dissolved in methylene chloride at 0° C.

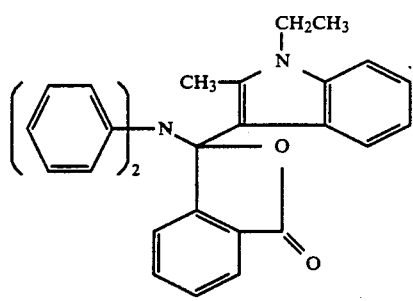

Foaming occurred. After 15 minutes, the reaction solution was added to a stirred solution of sodium hydrogen sulfide hydrate (5 g) in methanol (50 ml) and stirred for 20 minutes. The mixture was diluted with ether (300 ml) and washed with water, brine and dried over calcium sulfate. Solvent removal yielded 5 g of a crude orange solid. Purification on 30/60 micron silica, activity I yielded 3.2 g of a cream colored solid. M/e 474.6; Anal: Calc for $N_2OSC_{31}H_{26}$: C, 78.45; H, 5.52; N, 5.90; S, 6.76. Found: C, 78.05; H, 6.01; N, 5.36; S, 6.42.

EXAMPLE 26

Preparation of the compound having the formula

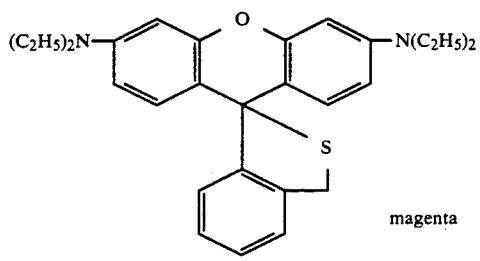

The acetoxymethyl derivative of Rhodamine B (0.5 g) having the formula

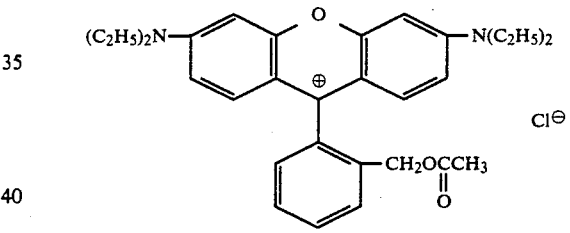

was heated to reflux with phosphorus pentasulfide (0.3 g) and pyridine (20 ml) for 2 hours. Ethyl ether (100 ml) was added to the warm solution and the residue triturated with ether (4×30 ml). The combined ether extracts were chromatographed on a silica column using hexane eluent to give 200 mg of the title compound as a tan solid. NMR ($CDCl_3$, TMS) 7.7–6.1 (10H, m) 4,5 (s, 2H), 3.2 (q, 8H) and 1.2 (t, 12H). M/e (FAB) $MH^+ = 445.6$

EXAMPLE 27

Preparation of the compound having the formula

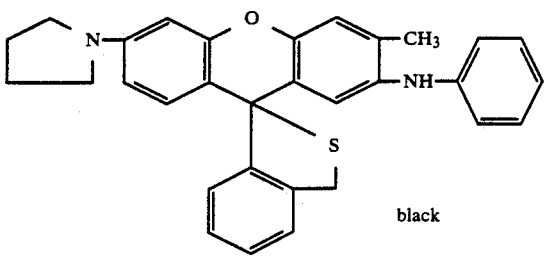

(a) A solution of 25 g (52.7 mmole) of the following lactone

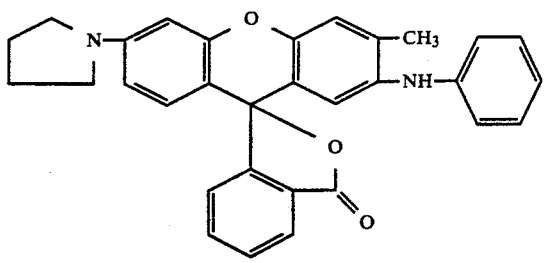

in 175 ml of dry tetrahydrofuran was added to a slurry of 7.97 g (0.21 mole) of lithium aluminum hydride in 250 ml of dry tetrahydrofuran under an atmosphere of nitrogen at room temperature. After addition, the mixture was allowed to stir at room temperature for 15 minutes then heated at reflux for 2 hours. The mixture was cooled to room temperature and then treated successively with 8 ml water, 8 ml 15% aqueous sodium hydroxide solution and 24 ml water.

The precipitated salts were filtered and washed with a small amount of tetrahydrofuran. The filtrate was evaporated under reduced pressure and the residue dissolved in 200 ml ethylene chloride, washed with ½-saturated sodium chloride solution (2×200 ml) and dried over sodium sulfate. The solvent was evaporated under reduced pressure to afford a light-brown oil. This oil was triturated in 100 ml of absolute ethanol, heated at reflux at which point crystallizatin occurred. The mixture was cooled in an ice bath, the product filtered, washed with a small amount of ethanol and dried in vacuo to give 20.5 g. (84% by weight) of the intermediate having the formula

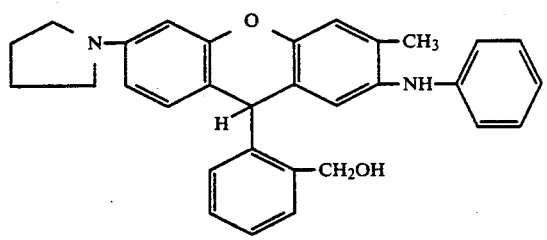

Hydrogen bromide was bubbled into 50 ml anhydrous methanesulfonic acid for 20 minutes at room temperature. Then 9.25 g (0.02 mole) of the intermediate of step (a) was added portionwise ovr a period of 2 to 3 minutes. The mixture was allowed to stir overnight at room temperature, then diluted with 100 ml chloroform, cautiously poured into 500 ml aqueous 5% sodium bicarbonate solution and transferred to a separatory funnel. The lower chloroform layer was separated, washed with 5% sodium bicarbonate solution (1×100 ml), ½-saturated sodium chloride solution (2×200 ml) and dried over magnesium sulfate. The magnesium sulfate was removed by filtration and the filtrate treated with 10 g silica gel to remove unreacted material. The silica gel was removed by filtration and the solvent evaporated from the filtrate under reduced pressure to afford an oil which was triturated in 100 ml of hot ethanol to induce crystallization. The mixture was cooled in an ice bath. The crystalline material was filtered, washed with a small amount of ethanol and dried in vacuo to give 9.84 g (94% by weight yield) of the following intermediate as an off-while solid.

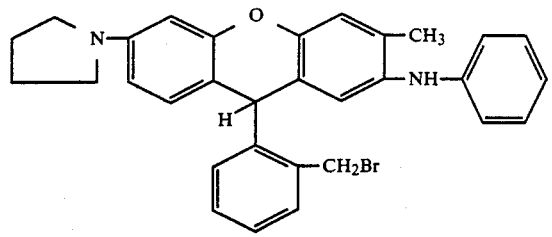

(c) To a mixture of 525.5 mg (1.0 mmole) of the intermediate prepared in step (b) in 10 ml ethyl acetate was added 0.1 ml (100 mg, 1.1 mmole) of thiolpropionic acid and 0.155 ml (112 mg, 1.1 mmole) of triethylamine. The mixture was gently heated under an atmosphere of nitrogen. TLC on silica using 1:1 ethylene chloride/hexane after 4 hours indicated 75% conversion. Another 0.05 ml (approximately 50 mg., 0.55 mmole) of thiolpropionic acid and 0.078 ml (56 mg, 0.55 mmole) of triethylamine was added and the mixture allowed to stir under gentle reflux overnight under an atmosphere of nitrogen. TLC after overnight reflux showed very little starting material. The mixture was filtered to remove the triethylamine hydrobromide and washed with a small amount of ethyl acetate. The ethyl acetate solution was washed with water (2×25 ml), 5% sodium bicarbonate solution (3×25 ml), saturated sodium chloride solution and then dried over sodium sulfate. The mixture was filtered, the solvent evaporated from the filtrate under reduced pressure and the residue dried under high vacuum to give 572.6 mg of the following intermediate

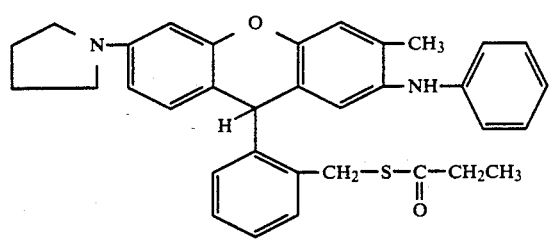

(d) A solution of 102.6 mg (0.19 mmole) of the intermediate prepared in step (c) in 10 ml methanol was treated with 50 mg (0.2 mmole) of o-chloranil. The mixture was heated to reflux for 2 hours. TLC indicated that conversion was substantially complete. Then 0.6 ml of aqueous 1.0 N sodium hydroxide solution was added and refluxing was continued for another hour. After cooling to room temperature, the solvent was evaporated under reduced pressure. The residue was dissolved in about 50 ml ether and filtered to remove a small amount of insoluble material. The ether solution was washed with water (1×50 ml), with saturated sodium chloride solution (3×50 ml) and then dried over sodium sulfate. The solvent was evaporated affording the title compound as a light-green amorphous solid.

A small amount of this solid was dissolved in ethylene chloride/methanol solution. Addition of acetic acid did not make the solution any darker in color, but upon addition of $HgCl_2$/pyridine, the solution turned black.

Illustrative of other compounds of the present invention are those of the following formulae:

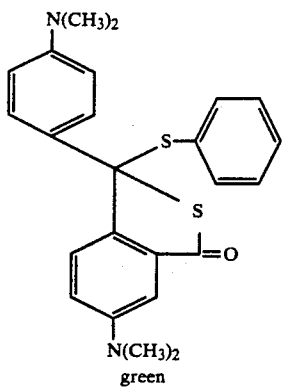

green

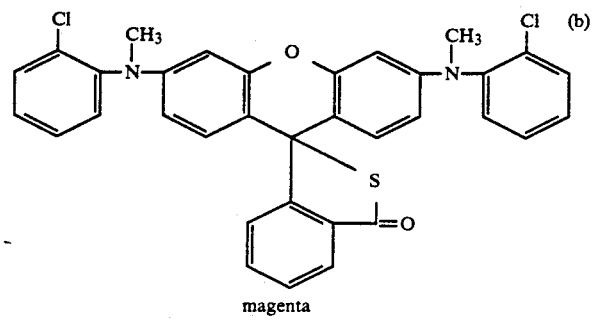

magenta

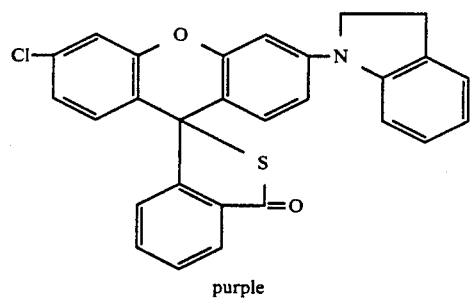

purple

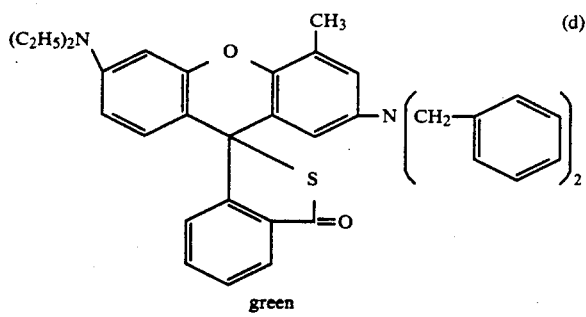

green

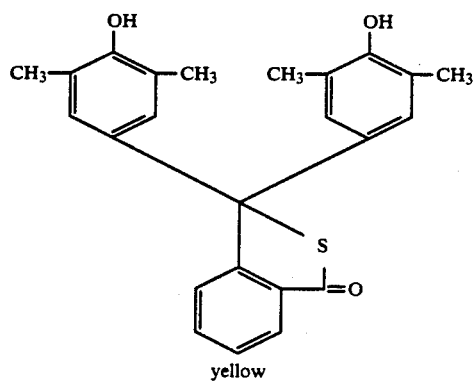

yellow

As mentioned previously, the subject dye precursors exhibit a preference for certain heavy metal ions, particularly, silver ion to give the metal complexes of the formulae

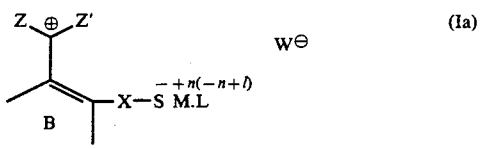

wherein X, b, Z and Z' have the same meaning given above, M is silver, mercury, gold of palladium, L represents a ligand or group of ligands, n is 1, 2, 3 or 4 and W is an anion; and in a preferred embodiment give the following complexes

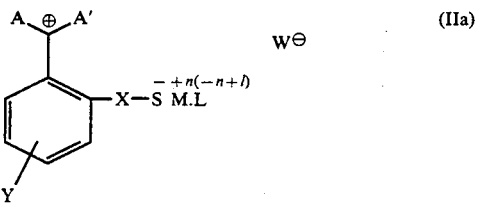

wherein X, Y, A and A', L, M, n and W have the same meaning given above. Preferably, X is

and M is Ag.

The anion W associated with the foregoing compounds may be any suitable single atomic ion or ionic group composed of a plurality of atoms having a negative charge, for example, halide such as chloride, bromide or iodide, nitrate, tetrafluoroborate, perchlorate, periodate, acetate, oxalate, tosylate, sulfate, methane sulfonate, methane hydrogen disulfonate, m-benzene hydrogen disulfonate, trifluoroacetate, hexafluoroacetate, hexafluorophosphorate, azide, trifluoromethane sulfonate, behenate, laurate, and so forth. The ligand L may be any suitable single ion or ionic group having a total negative charge to complete any additional valence of M when n is greater than $+1$. L may be any of the ions or ionic groups enumerated for W and can include additional molecule(s) of said dye precursor.

To illustrate the specific reactivity to Lewis acid materials versus Bronsted acids, solutions of the thiophthalides of the compounds of the above Examples 1 to 16 were found to be substantially colorless in glacial acetic acid solution but found to colorize to their chromophore color upon the addition of methanolic silver nitrate solution. In comparison, the oxygen analogs, i.e., the corresponding phthalides were colored in acetic acid in the absence of $Ag^+$. Also, when a 0.02 molar solution of the thiophthalide compound of Example 1 and a 0.02 molar solution of a silver uracil complex were mixed at pH 14, the solution was slightly pink. Dropping the pH to about 4 to 5 with acetic acid or with hydrochloric acid generated the chromophore color of the dye by making $Ag^+$ available from the silver uracil complex. In comparison, the addition of acetic acid or hydrochloric acid in the absence of the silver uracil complex did not generate color.

Dithiodichlorofluorane when treated with silver nitrate solution formed a yellow precipitate which rapidly turned brownish yellow. It was determined that the brownish yellow material was a silver sulfide and that the dithiophthalide apparently was converted to the thiophthalide due to the presence of the corresponding thiophthalide in the supernatant solution. It was also noted that the new material did not colorize with silver nitrate.

In a further experiment to determine chromophore color formation with Lewis acids, the thiophthalides of Examples 1 to 12, 14 and 16 and the dithiophthalides corresponding to the thiophthalides of Examples 1, 2, 4 and 9 were placed on silica TLC plates and spot tested with solutions of silver nitrate, mercurous chloride, gold chloride and palladium chloride, respectively. It was found that all of the above-denoted compounds gave their chromophore color with all of these Lewis acids. The thiophthalides of Examples 1 to 6, 9 to 11 and 16 when tested in the same manner with mercuric chloride also gave their chromophore color though only slight color was formed with the thiophthalides of Examples 9 and 11 and also with the dithiophthalide corresponding to the thiophthalide of Example 9. In comparison, when diphenyldithiophthalide was tested in the same manner, it formed brown-orange with palladium and gold, brown-gray with silver and showed no change with mercurous chloride. Dithiodichlorofluorane when tested in the same manner formed yellow with palladium, brown with gold, yellow-gray with silver and showed no change with mercurous chloride.

The thiophthalides of Examples 4, 6 to 12, 14 and 16 and the dithiophthalides corresponding to the thiophthalides of Examples 4 and 9 also were tested with an anhydrous aluminum chloride solution. No color change was observed with the thiophthalides of Examples 4, 6 and 9. The thiophthalides of Examples 7, 8, 10, 12, 14 and 16 gave their chromophore color, though Examples 7, 12 and 14 gave only slight color as did diphenyldithiophthalide and dithiodichlorofluorane. Aluminum ion added as a salicylate or methoxide complex did not impart color. Presumably due to the formation of a carbonium complex with aluminum rather than a lactone complex, Example 11 gave yellow rather than the blue chromophore color. The dithiophthalide of Example 4 showed no change and the dithiophthalide of Example 9 went colorless which was determined to result from the conversion of the dithiophthalide to the corresponding thiophthalide.

The dithiodichlorofluorane gave slight yellow coloration with boron trifluoride etherate which presumably also was due to the formation of a carbonium ion complex. The thiophthalides of Examples 10 and 16 gave their chromophore color. However, the thiophthalides of Examples 4, 9 and 11 showed no color change and the dithiophthalide corresponding to the thiophthalide of Example 4 also showed no change.

The thiophthalides of Examples 1 to 12, 14 and 16 and the dithiophthalides corresponding to the thiophthalides of Examples 1, 2, 4 and 9 showed no color change on silica TLC plates in the absence of a Lewis acid nor did those compounds exhibit any color change when treated with Bronsted acids, such as, glacial acetic acid and 2,5-diisopropylsalicylic acid. It was found, however, that the phthalides used as the starting materials for the subject thio- and dithiophthalides gave their chromophore color with these Bronsted acids and on silica TLC plates. In contrast, diphenylphthalide and fluoresceinchloride gave no color change on silica or with these Bronsted acids nor did their corresponding dithiophthalides under the same conditions.

As mentioned previously, the subject compounds find various utilities including use as dye imaging compounds in imaging systems employing silver salts. As an illustration, the thiophthalide compound of Example 1 and 4-methylphenyl hydroquinone were disposed in a layer on a polyester support under a photosensitive silver halide layer. After imagewise photoexposure, an aqueous processing composition comprising a boric acid/sodium hydroxide buffer containing 3% by weight of benzylaminopurine was applied in a conventional manner in a layer between the exposed photosensitive element and a spreader sheet, and after heating at 75° C. for 10 to 20 minutes, a magenta image was formed with gray highlights.

As an illustration of the use of the subject compounds in thermographic image-recording materials as disclosed and claimed in aforementioned U.S. patent application Ser. No. 935,534, an image-recording element was fabricated by coating the following layers on a transparent polyethylene terephthalate support:

(1) a layer comprising the thiophthalide compound of Example 1 coated at a coverage of 50 mgs/ft$^2$, silver behenate coated at a coverage of 15 mgs/ft$^2$ silver and polyvinylbutyral coated at a coverage of 50 mgs/ft$^2$ and (2) a topcoat layer of polyvinylbutyral coated at a cover of about 100 mg/ft$^2$.

This image-recording element (coated surface) was placed against the printed surface of an original to be copied and then imaged using a thermographic office copier to give a transparency having a magenta image. The high intensity radiation provided by the thermographic copier is preferentially absorbed by the infrared absorbing characters of the original, and the absorbed radiation is converted to heat which melts the silver behenate to provide Ag$^+$ for reaction with the thiophthalide compound whereby a magenta image as formed in the image-recording element corresponding to the printed pattern of the original. The maximum and minimum transmission densities measured for the imaged element using a Macbeth transmission densitometer were 0.10/0.04 (R), 1.31/0.05 (G) and 0.18/0.05 (B).

Another image-recording element was prepared by coating the following layers on a transparent polyethylene terephthalate support:

(1) a layer comprising 3,5-diisopropylsalicyclic acid coated at a coverage of 50 mgs/ft$^2$, silver behenate coated at a coverage of 12 mgs/ft$^2$ silver, polyvinylbutyral coated at a coverage of 125 mgs/ft$^2$ and 1,4-butanediol diglycidyl ether coated at a coverage of 6.25 mgs/ft$^2$;

(2) a layer comprising the Compound of Example 9 coated at a coverage of 50 mgs/ft$^2$, polyvinylbutyral coated at a coverage of 100 mgs/ft$^2$ and 1,4-butanediol diglycidyl ether coated at a coverage of 5 mgs/ft$^2$; and (3) a topcoat layer of cellulose acetate coated at a coverage of 100 mgs/ft$^2$.

This image-recording element was imaged in the same manner described above to give a transparency containing a blue image. The maximum and minimum transmission densities measured for the imaged element were 0.02/1.93(R), 0.30/0.86(G) and 0.04/0.19(B).

Since certain changes may be made in the herein described subject matter without departing from the scope of the invention herein involved, it is intended that all matter contained in the above description and examples be interpreted as illustrative and not in a limiting sense.

What is claimed is:

1. A compound of the formula

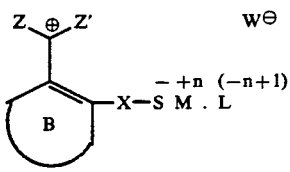

wherein X is

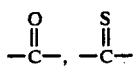

or —CH$_2$—; ring B represents a carbocyclic aryl ring, substituted or unsubstituted, or a heterocyclic aryl ring; Z and Z' taken individually represent the moieties to complete the auxochromophoric system of a diarylmethane or a triarylmethane dye and Z and Z' taken together represent the bridged moieties to complete the auxochromophoric system of a bridged triarylmethane dye; M is silver, mercury, gold or palladium; L represents a ligand or group of ligands, n is 1, 2, 3 or 4 and W is an anion.

2. A compound as defined in claim 1 wherein X is

3. A compound as defined in claim 1 wherein X is

4. A compound as defined in claim 1 wherein X is —CH$_2$—.

5. A compound as defined in claim 1 wherein n is 1.

6. A compound as defined in claim 1 wherein M is silver.

7. A compound as defined in claim 1 wherein Z and Z' are taken together and represent the bridged moieties to complete the auxochromophoric system of a bridged triarylmethane dye.

8. A compound as defined in claim 7 wherein B represents said carbocyclic aryl ring.

9. A compound as defined in claim 7 wherein said carbocyclic aryl ring is a benzene ring.

10. A compound of the formula

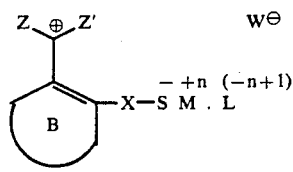

wherein X is

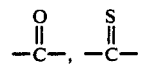

or —CH$_2$—; ring B represents a carbocyclic aryl ring, substituted or unsubstituted; Z and Z' taken individually represent the moieties to complete the auxochromophoric system of a diarylmethane or a triarylmethane dye and Z and Z' taken together represent the bridged moieties to complete the auxochromophoric system of a bridged triarylmethane dye; M is silver or gold; L represents a ligand or group of ligands, n is 1, 2, 3 or 4 and W is an anion.

* * * * *